United States Patent [19]
Falcoff et al.

[11] Patent Number: 4,977,853
[45] Date of Patent: Dec. 18, 1990

[54] NON-CONTACT WET OR DRY FILM THICKNESS MEASURING DEVICE

[75] Inventors: Allan F. Falcoff, Lake Orion, Mich.; Frank S. Fountain, Wilmington, Del.; Donald K. Pusey, West Grove, Pa.

[73] Assignee: E. I. Du Pont de Nemours and Company, Wilmington, Del.

[21] Appl. No.: 360,054

[22] Filed: Jun. 1, 1989

[51] Int. Cl.⁵ .......................... G01B 7/10; G01B 11/14
[52] U.S. Cl. ..................................... 118/665; 73/601; 118/712; 324/230
[58] Field of Search ..................... 118/664, 665, 712; 425/141; 264/40.2; 73/601, 597; 324/230; 250/201, 561

[56] References Cited

U.S. PATENT DOCUMENTS

| | | | |
|---|---|---|---|
| 3,237,446 | 3/1966 | Wood | 73/601 |
| 3,884,076 | 5/1975 | Studer | 324/230 |
| 4,167,878 | 9/1979 | Bottcher et al. | 73/601 |
| 4,398,421 | 8/1983 | White | 73/597 |
| 4,614,300 | 9/1986 | Falcoff | 239/71 |
| 4,702,931 | 10/1987 | Falcoff | 427/10 |
| 4,814,703 | 3/1989 | Carr et al. | 73/597 |
| 4,849,694 | 7/1989 | Coates | 324/230 |

FOREIGN PATENT DOCUMENTS

| | | | |
|---|---|---|---|
| 3016458 | 11/1981 | Fed. Rep. of Germany | 118/665 |
| 60-144603 | 7/1985 | Japan | 324/230 |
| 598972 | 3/1978 | U.S.S.R. | 324/230 |

OTHER PUBLICATIONS

"Measuring Thicknesses of Coatings on Metals", NASA Tech Briefs, May/Jun. 1986, pp. 94, 96.
Cyber Optics Bulletin, "Point Range Sensors", 1986.

Primary Examiner—James C. Housel
Attorney, Agent, or Firm—Hilmar L. Fricke

[57] ABSTRACT

A device for measuring the thickness of a wet or dry paint film applied on a substrate without contacting the film is disclosed. The device uses an optical sensor positioned centrally and coaxially with an inductive eddy-current proximity sensor. The optical sensor measures the distance between the device and the upper surface of the paint film at specular reflection angle. The proximity sensor measures the distance between the device and the upper surface of the substrate. The two distances measured, when compared, produce the film thickness value. The device is capable of accurately measuring thickness of various paint films, such as flat, glossy and metal-flake containing paint films.

11 Claims, 4 Drawing Sheets

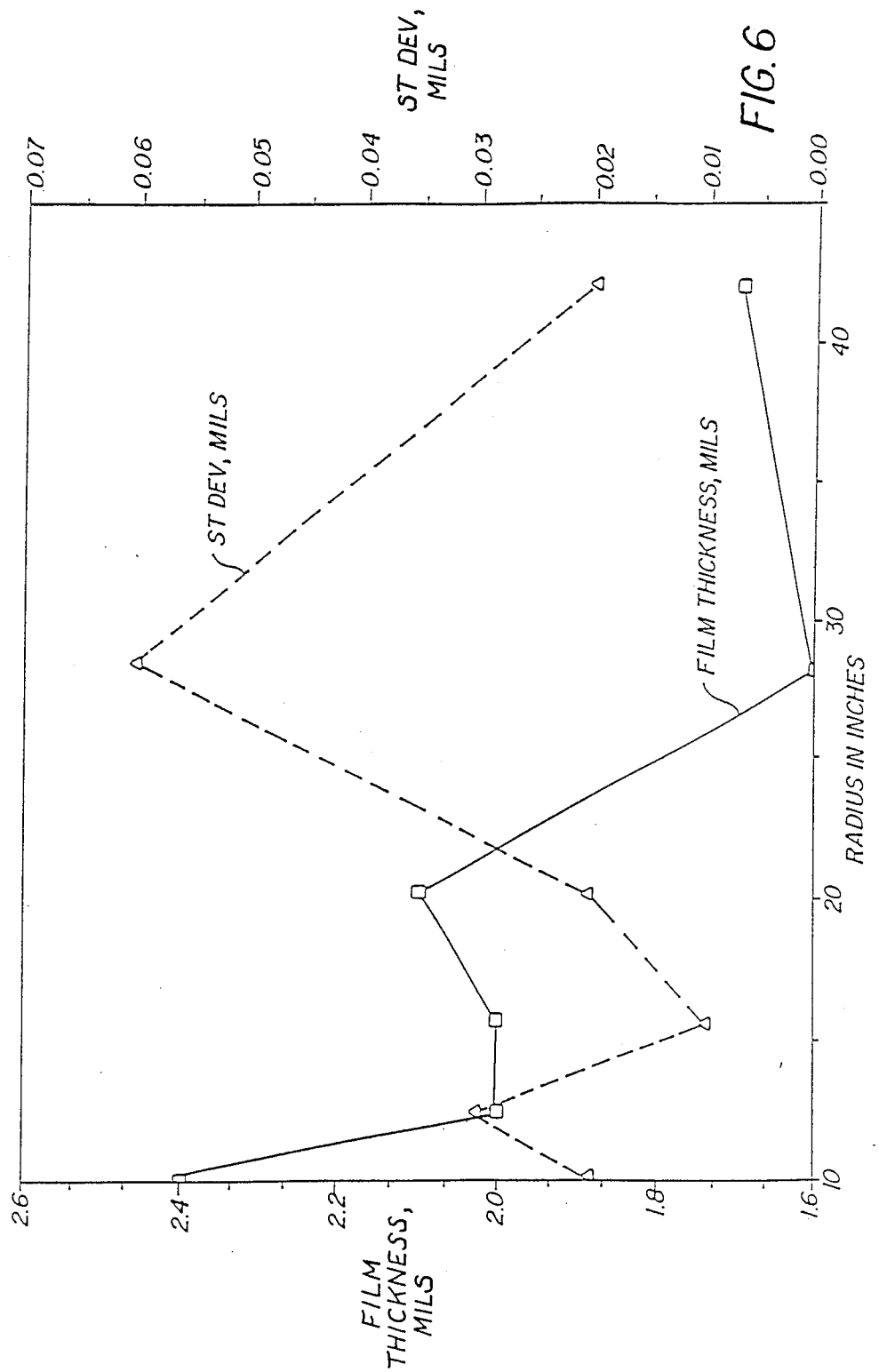

NON-CONTACT WET OR DRY FILM THICKNESS MEASURING DEVICE

BACKGROUND OF THE INVENTION

The present invention is directed to a device for measuring the thickness of a film applied on a substrate without contacting the film itself. In particular, the device may be used in combination with a spray machine for measuring the thickness of a wet or dry paint film sprayed on a metal substrate, and which controls the thickness of the paint film to be applied to the next substrate.

In the spray application of many paints, a relatively thin film is formed near the edge of the article being coated and is substantially thicker in the center of the article. This difference in thickness of the paint film results in appearance changes from the center to the edge of the article. This is a problem in the coating of articles, such as auto or truck body panels, in which a uniform appearance is desired, and in particular is a problem for paint panels which are used as color standards in laboratories, paint manufacturing plants and automotive and truck assembly plants. In particular, rejects of paint panels to be used for color standards can be as high as 50% of the panels coated for such uses.

An example of a spray machine is shown in Falcoff, U.S. Pat. No. 4,614,300, issued Sept. 30, 1986. Many spray parameters are set and automatically controlled by this machine with the exception of the paint film thickness.

Another example of an improved paint spraying device with wet film thickness measurement and feedback control is shown in Falcoff, U.S. Pat. No. 4,702,931, issued Oct. 27, 1987. However, this device has the disadvantage that the sensors for measuring the distance from the device to the article being coated are disposed on opposite sides of the substrate. This severely limits the use of this device in an assembly line work where series of articles to be coated are generally conveyed in succession. In particular, where the articles being painted are auto or truck body panels, it is virtually impossible to position the sensors on both sides of the panels.

Another device for measuring thickness of coatings on substrates is disclosed in "Measuring Thicknesses of Coatings on Metals," NASA Tech Briefs, May/June 1986, pages 94 & 96. This reference discloses the use of a triangulation optical sensing arrangement by using a helium-neon laser with an angle sensing photo-detector in a side-by-side configuration with an inductive proximity sensor. However, this arrangement has two disadvantages. First, since the pair of sensors are disposed side-by-side, the angular orientation to the substrate surface must be precise in order to obtain reproducible results. A slight angular misalignment causes the distance from each sensor to the surface to change, resulting in an incorrect coating thickness measurement. Second, the optical sensor, as described in the reference, utilizes a beam of light normal to the surface and detects light from the surface at an angle. Accordingly, the performance of the sensor is dependent on the reflectivity and scattering properties of the film surface. Since some scattered light must be present for the optical detector to function, a perfect reflecting surface would not be measurable with this configuration. For example, a glossy surface, such as that found in automotive finishes, might be difficult to measure, particularly in bright ambient light.

In view of the above, there is a need in the art for a non-contact wet or dry film thickness measuring device which does not have the disadvantages associated with the conventional devices, and which controls the thickness of the paint film applied on the substrates.

OBJECT AND SUMMARY OF THE INVENTION

The principal object of the present invention is to provide a device for measuring the thickness of a wet or dry film applied on a substrate without contacting the film which overcomes the disadvantages associated with conventional devices.

Another object of the present invention is to provide a device for measuring the thickness of a wet or dry film applied on a substrate without contacting the film which may be used in combination with a device for controlling the thickness of film.

Yet another object of the present invention is to provide a device for measuring the thickness of a wet or dry film applied on a substrate without contacting the film which is not dependent on the reflectivity and scattering properties of the film, and is thus insensitive to the color of the film.

An additional object of the present invention is to provide a device for measuring the thickness of a wet or dry film applied on a substrate without contacting the film in which the triangulation measurement is taken at the specular reflection angle.

Still an additional object of the present invention is to provide a device for measuring the thickness of a wet or dry film applied on a substrate without contacting the film by which paint film thickness measurement accuracies of 120 microns and better are achieved.

Still yet another object of the present invention is to provide a device for measuring the thickness of a wet or dry film applied on a substrate without contacting the film in which the sensitivity of the measurement to angular orientation to the substrate surface is greatly reduced.

In summary, the main object of the present invention is to provide a device for measuring the thickness of a wet or dry film applied on a substrate without contacting the film which accurately measures the thickness of different types of paint films, such as glossy, flat and metal-flake containing paint films.

BRIEF DESCRIPTION OF THE DRAWINGS

The above and other objects and advantages and novel features of the present invention will become apparent from the following detailed description of the preferred embodiment of the invention illustrated in the accompanying drawings, in which:

FIGS. 5 and 6 are graphical representations of experimental data of paint film thickness measurements taken on two curved panels having different radii of curvature by using the device of the present invention.

DETAILED DESCRIPTION OF THE INVENTION

Figure 2:
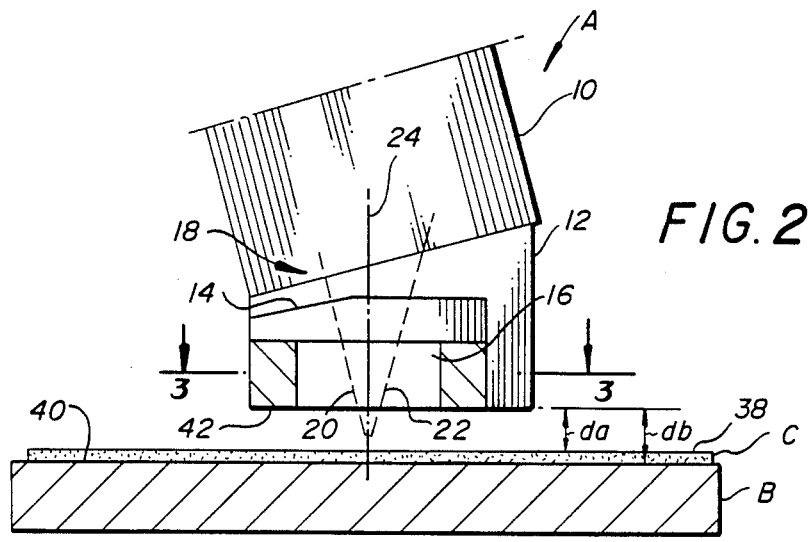
FIG. 2 is an elevational view, partially in section, illustrating the positions of the optical triangulation sensor and the inductive eddy-current proximity sensor in relation to the paint coated substrate.

Referring now to FIG. 2, the non-contact wet or dry film thickness measuring device generally indicated as A, includes a triangulation optical sensor 10 mounted on a support member 12 above inductive eddy-current proximity sensor 14 in a coaxial relationship. The device A would normally be mounted on a mechanical placement device, such as a computer controlled robotic arm, to position the device relative to a substrate or article for measuring the paint film thickness. As FIG. 2 illustrates, device A has been positioned above a substrate B sprayed with a paint film C thereon. (It should be noted that only the parts necessary for an understanding of the invention are shown and described).

The proximity sensor 14 is generally hollow and defines therein a vertically extending slot 16 through which a laser beam 18 or the like is projected from optical sensor 10. Preferably, slot 16 has a dimension of 0.49 inch×0.10 inch. In FIG. 2, numeral 20 indicates the incident beam and 22 indicates the beam reflected from film C. Similarly, numeral 24 represents the central axis of proximity sensor 14.

Figure 4:
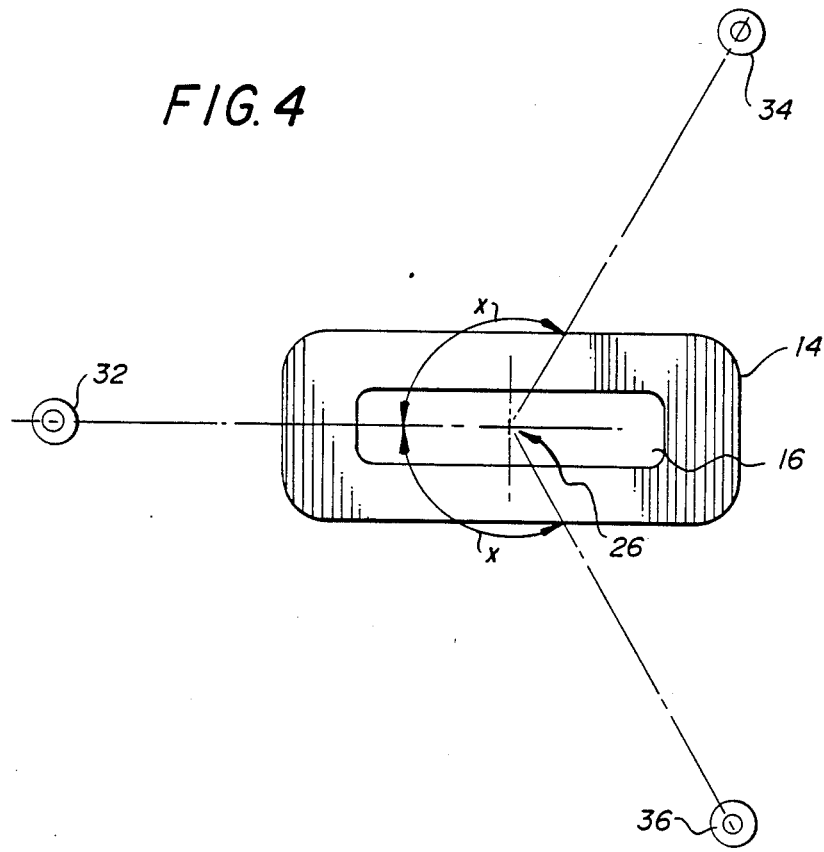
FIG. 4 is a view similar to FIG. 3, showing an alternate embodiment without the substrate, which includes three auxiliary proximity sensors.
Figure 3:
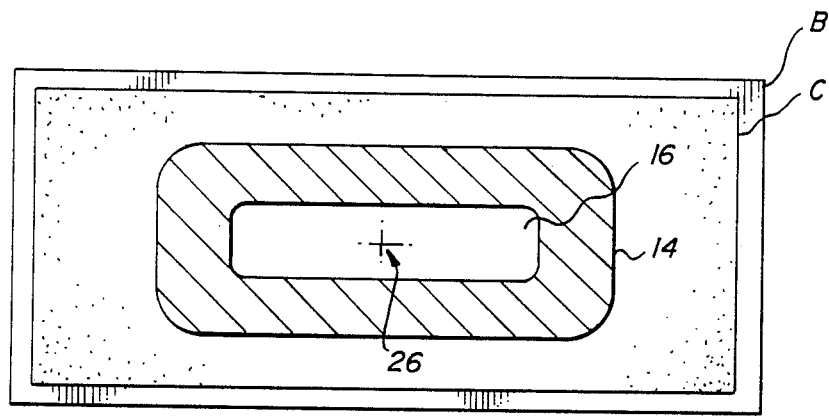
FIG. 3 is an enlarged sectional view taken along line 3—3 of FIG. 2.

As best shown in FIGS. 3 and 4, proximity sensor 14 is generally "racetrack" shaped. It should be noted, however, that it can alternatively be oval or rectangular in shape. In FIG. 3, numeral 26 indicates the position of laser beam 18 at the center of proximity sensor 14 lying coincident with axis 24 thereof (shown in FIG. 2).

Figure 1:
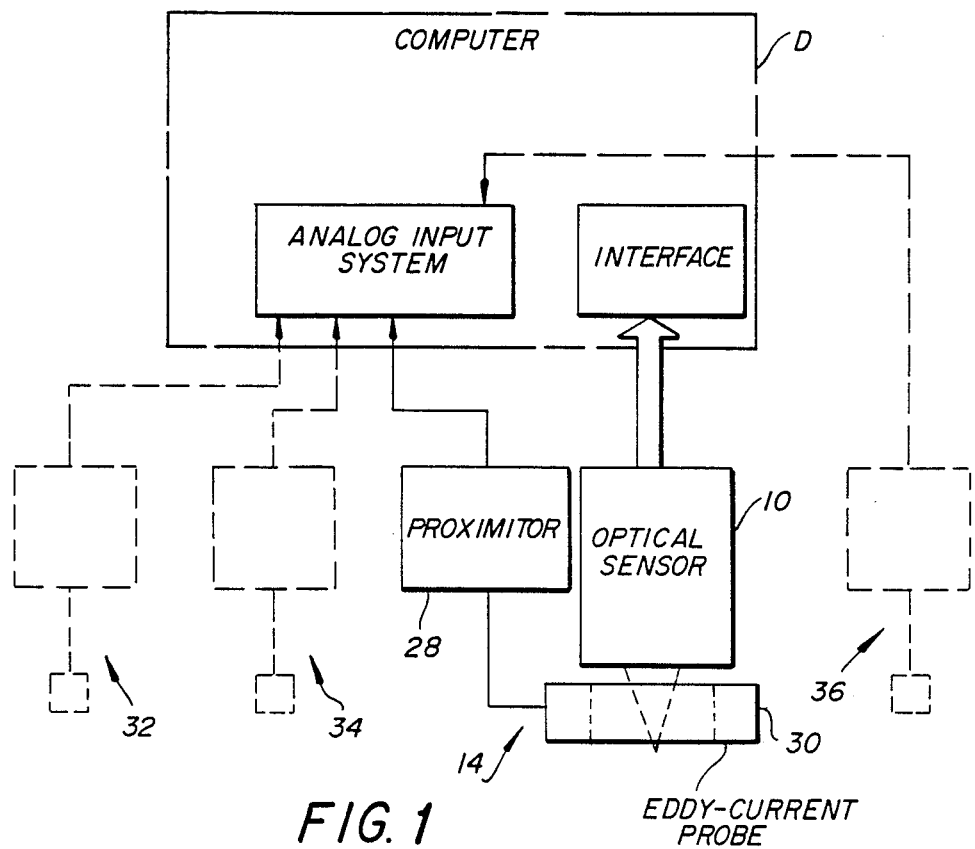
FIG. 1 is a schematic illustration of the device of the present invention, showing three auxiliary inductive eddy-current proximity sensors in phantom lines.

As schematically illustrated in FIG. 1, optical sensor 10, and proximity sensor 14 including a proximitor 28 and inductive eddy-current probe 30, interface via conventional means, such as analog input systems, with computer D. Also shown in FIG. 1 are three auxiliary inductive eddy-current proximity sensors 32, 34 and 36, which may be employed in addition to the racetrack shaped proximity sensor 14, to greatly improve the efficiency of device A, as discussed below.

FIG. 4 illustrates the alternate embodiment in which three auxiliary proximity sensors 32, 34 and 36 are disposed around proximity sensor 14. The auxiliary proximity sensors are equilaterally spaced in a circular fashion at an angular distance of about 120° relative to proximity sensor 14, indicated by angle x in FIG. 4. The proximity sensors 32, 34 and 36, are each positioned at a preferable distance between one and two inches from central axis 24 (shown in FIG. 2).

Preferably, auxiliary proximity sensors 32, 34 and 36 are each cylindrically shaped, and are available from Bentley Nevada, Minden, Nev. 89423, as Model Number 21500-00-08-10-02, used with Model Number 18745-03 Proximitors and Model Number 21747-040-00 extension cables. Similarly, the oval racetrack shaped proximity sensor 14 is also available from the same company by citing Inquiry Number 10147. The triangulation optical sensor 10 may be a Point Range Sensor, Model Number PRS-50, available from CyberOptis Corporation, Minneapolis, Minn. 55414. A model DT-2814 Analog Input System available from Data Translation, Inc., Marlboro, Mass., may be used to interface the Bentley sensors to an IBM PC or a compatible personal computer.

Although the alternate embodiment shown in FIG. 4 utilizes three auxiliary proximity sensors in a circular fashion, it would be apparent to those of ordinary skill in the art that in order to improve efficiency of the device, more than three auxiliary sensors in a different pattern, for example, rectilinear pattern, may be used to precisely define a surface, such as a curved surface, for greatly improving the accuracy of the measurements.

A critical aspect of the invention to be kept in mind, is the orientation of optical sensor 10 relative to substrate B (see FIG. 2). In particular, the orientation of incident and reflected beams 20 and 22, respectively, of laser beam 18 have been selected so as to obtain the triangulation measurement at the specular reflection angle. Thus the incident beam 20 and the reflected beam 22 are symmetrically disposed about an optical axis of symmetry which is coaxial with proximity sensor axis 24. This arrangement leads to making the measurement substantially less dependent on the scattering properties of film C. The specific configuration disclosed herein has demonstrated effective performance of the device when measuring various types of paints, such as glossy, flat and metal-flake containing paints.

Although not shown, the device of the present invention may include means for controlling the film thickness. An example of this type of device is disclosed in Falcoff, U.S. Pat. No. 4,702,931, the entire disclosure of which is incorporated herein by reference. The film thickness control device would be in operable association with the device A of the present invention in order to vary the amount of paint to be applied to a next substrate in accordance with the paint film thickness measurement taken on a previous substrate.

Typically, in an operation for painting auto or truck body panels or the like, series of articles are spray painted automatically by a machine, such as a robot, in succession, to obtain a uniform paint film thickness throughout the surfaces of the articles. However, several factors are known to cause variations in film thicknesses. Some of the factors include paint viscosity, paint flow rate, atomization pressure at the paint nozzle, various temperature gradations in the surroundings, air flow, and humidity. Since these factors tend to fluctuate, the film thickness may vary tremendously in a given period of operation. Therefore, it becomes critical that the paint film thickness be monitored at regular, desirable intervals. At any time, when a variation in the film thickness is detected, one or more of these factors may be adjusted in order to obtain the desired paint film thickness.

In use, the device A of the present invention is positioned above metal substrate B with paint film C sprayed thereon. Optical sensor 10 measures a distance $d_a$ from device A to upper surface 38 of paint film C, and proximity sensor 14 measures a distance $d_b$ from the device to upper surface 40 of metal substrate B. The measurements $d_a$ and $d_b$ are fed into computer D and compared to determine the paint film thickness $d_c$.

The above can be illustrated as follows:
$d_a$=distance from device A to paint film surface 38
$d_b$=distance from device A to substrate surface 40
Thickness of paint film $(d_c) = d_b - d_a$.

It would be apparent to those of ordinary skill in the art that it is critical that lower surface 42 of proximity sensor 14 be kept parallel to film surface 38, as any slight variation would produce an inaccurate reading. In order to eliminate any misalignment or to overcome the angular error, the second embodiment shown in FIG. 4 may be used. In this embodiment, the auxiliary proximity sensors 32, 34 and 36, may be positioned in the plane of lower surface 42 of proximity sensor 14, thereby attaining extremely accurate alignment with the plane of paint film surface 38. In particular, any angular alignment of surface 42 may be corrected by measuring the distance to surface 38 from each of the three auxiliary sensors 32, 34 and 36, computing the angular error, and then correcting the angular position in accordance therewith.

The alternate embodiment using one proximity sensor 14 and three auxiliary proximity sensors 32, 34 and 36, also permits accurate measurements on curved surfaces, frequently found on automobile body panels. As shown in FIG. 4, by placing device A above the curved surface of a substrate, the three auxiliary proximity sensors 32, 34 and 36 measure any angular alignment of surface 42 of sensor 14 relative to surface 38 of film C, as described above. The proximity sensor 14 then makes another distance measurement from the device to the upper surface of the substrate and compares it with the measurements taken by auxiliary proximity sensors 32, 34 and 36, to calculate the radius of curvature of the surface in three directions. The theoretical plane at the center point of proximity sensor may then be calculated to insure that its lower surface 42 is in proper alignment, i.e., parallel, to upper surface 38 of the paint film.

Figure 5:
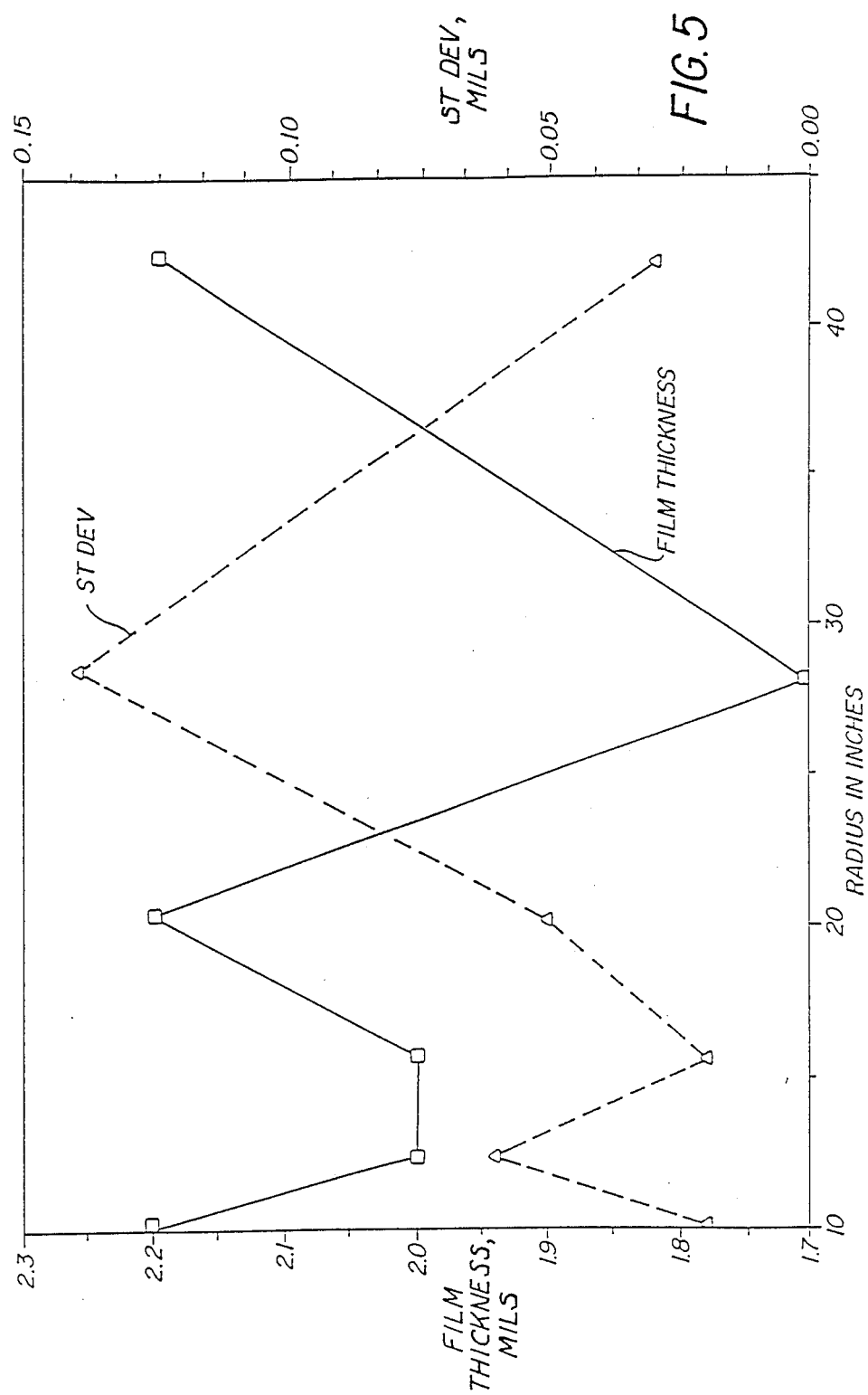

The device of the present invention was used to measure paint film thicknesses of two test panels each having six different radii of curvature. The results obtained are provided below in Tables I and II, and the measured data are shown graphically in FIGS. 5 and 6.

TABLE I

| | (Panel #1) | | |
|---|---|---|---|
| Radius | Measured Film Thickness | Standard deviation | N |
| 42.0 inches | 2.2 mil | 0.03 mil | 36 |
| 28.1 inches | 1.7 mil | 0.14 mil | 36 |
| 20.1 inches | 2.2 mil | 0.05 mil | 36 |
| 15.6 inches | 2.0 mil | 0.02 mil | 36 |
| 12.3 inches | 2.0 mil | 0.06 mil | 36 |
| 10.1 inches | 2.4 mil | 0.02 mil | 36 |

TABLE II

| | (Panel #2) | | |
|---|---|---|---|
| Radius | Measured Film Thickness | Standard deviation | N |
| 42.0 inches | 1.7 mil | 0.02 mil | 36 |
| 28.1 inches | 1.6 mil | 0.06 mil | 36 |
| 20.1 inches | 2.1 mil | 0.02 mil | 36 |
| 15.6 inches | 2.0 mil | 0.01 mil | 36 |
| 12.3 inches | 2.0 mil | 0.03 mil | 36 |
| 10.1 inches | 2.4 mil | 0.02 mil | 36 |

N = Number of readings averaged

As can be observed from the above, the readings taken by the present device are consistent at various radii of curvature, with a standard deviation of only from about 0.01–0.14.

While this invention has been described as having a preferred design, it is understood that it is capable of further modifications, uses and/or adaptations of the invention following in general the principle of the invention and including such departures from the present disclosure as may come within known or customary practice in the art to which the invention pertains, and as may be applied to the essential features set forth, and as may fall within the scope of the invention or the limits of the appended claims.

What is claimed is:

1. A device for measuring the thickness of a film applied on a substrate without contacting the film, comprising;
   (a) first optical sensor means for measuring a first distance value between the top surface of the film and the device;
   (b) second inductive eddy-current proximity sensor means generally oval in shape and has a slot extending about a center axis thereof coaxial with said first means for measuring a second distance value between the top surface of the substrate and the device; and said optical sensor means is positioned centrally above said proximity sensor means and projects a light beam through said slot; and wherein the optical axis of symmetry is coaxial with the proximity sensor means axis and the beam intersects the proximity sensor means axis at the top surface of the film; and
   (c) said first and second means disposed on the same side of the substrate; and
   (d) means electrically connected with said first and second means for calculating the film thickness by comparing said first and second distance values.

2. The device of claim 1, wherein:
   (a) said optical sensor means is oriented in a manner so as to measure first distance value at the specular reflection angle of the beam.

3. A device for applying film to a substrate comprising:
   (a) means for applying the film to the substrate;
   (b) means for receiving a signal from a film thickness measuring device defined below and determining increase or decrease in the amount of film to be applied to a next substrate and transmitting a signal to said film applying means for controlling the amount of film to be applied; wherein the film thickness measuring device measures film thickness of a film applied on a substrate without contacting the film and comprises:
      (1) optical sensor means for measuring a first distance value between the top surface of the film and the device;
      (2) inductive eddy-current proximity sensor means coaxial with said optical sensor means for measuring a second distance value between the top surface of the substrate and the device, said proximity sensor having a central opening through which the optical sensor measures the first distance value whereby the proximity sensor does not interfere with the optical sensor;
      (3) said optical sensor means and said proximity sensor means disposed on the same side of the substrate; and
      (4) means electrically connected with said optical sensor means and said proximity sensor means for calculating the film thickness by comparing said first and second distance values and means for feeding a signal to the above adjusting means.

4. A device for measuring the thickness of a film applied on a substrate without contacting the film, comprising:
   (a) optical sensor means for measuring a first distance value between the top surface of the film and the device;
   (b) inductive eddy-current proximity sensor means coaxial with said optical sensor means for measuring a second distance value between the top surface of the substrate and the device, said proximity sensor having a central opening through which the optical sensor measures the first distance value whereby the proximity sensor does not interfere with the optical sensor;

(c) said optical sensor means and said proximity sensor means disposed on the same side of the substrate; and (d) means electrically connected with said optical sensor means and said proximity sensor means for calculating the film thickness by comparing said first and second distance values.

5. The device of claim 4, wherein:

(a) said proximity sensor means is hollow and generally rectangular in shape.

6. A device for measuring the thickness of a film applied on a substrate without contacting the film, comprising:

(a) optical sensor means for measuring a first distance value between the top surface of the film and the device;

(b) inductive eddy-current proximity sensor means coaxial with said optical sensor means for measuring a second distance value between the top surface of the substrate and the device, said proximity sensor having a central opening through which the optical sensor measures the first distance value whereby the proximity sensor does not interfere with the optical sensor;

(c) auxiliary sensor means spaced from said proximity sensor means for measuring a third distance value between the top surface of the substrate and the device;

(d) said optical sensor means, said proximity sensor means, and said auxiliary sensor means all disposed on the same side of the substrate;

(e) means electrically connected with said optical sensor means, said proximity sensor means, and said auxiliary sensor means for calculating the film thickness by comparing said first, second, and third distance values.

7. The device of claim 6, wherein:

(a) said proximity sensor means is hollow and generally rectangular in shape; and (b) said auxiliary sensor means is generally cylindrical in shape.

8. The device of claim 6, wherein:

(a) a plurality of said auxiliary sensor means are disposed around said proximity sensor means in a circular pattern.

9. The device of claim 8, wherein:

(a) said auxiliary sensor means are equilaterally spaced by an angular distance of about 120°.

10. The device of claim 8, wherein:

(a) at least three said auxiliary sensor means are disposed around said proximity sensor means.

11. The device of claim 6, wherein:

(a) said auxiliary sensor means includes at least one inductive eddy-current proximity sensor.

* * * * *

UNITED STATES PATENT AND TRADEMARK OFFICE
CERTIFICATE OF CORRECTION

PATENT NO. : 4,977,853

DATED : December 18, 1990

INVENTOR(S) : Allan F. Falcoff, Frank S. Fountain, Donald K. Pusey

It is certified that error appears in the above-identified patent and that said Letters Patent is hereby corrected as shown below:

Claim 3, Column 6, line 30, after "substrate:" insert --and--

Claim 3, Column 6, line 31, before "means" insert --adjusting--

Signed and Sealed this

Sixth Day of October, 1992

Attest:

DOUGLAS B. COMER

Attesting Officer

Acting Commissioner of Patents and Trademarks